United States Patent [19]
Zhong

[11] Patent Number: 5,370,631
[45] Date of Patent: Dec. 6, 1994

[54] METHOD AND APPARATUS FOR DE-AIRING THE HEART

[76] Inventor: Being-Tang Zhong, 5126 Calhoun, Apt. 10, Houston, Tex. 77021

[21] Appl. No.: 202,339

[22] Filed: Feb. 25, 1994

Related U.S. Application Data

[62] Division of Ser. No. 816,115, Jan. 2, 1992, Pat. No. 5,290,257.

[51] Int. Cl.⁵ ............................................. A61M 5/178
[52] U.S. Cl. ..................................... 604/212; 604/217; 604/316; 604/317; 604/187; 128/898
[58] Field of Search ............... 604/212, 213, 215, 216, 604/218, 187, 239, 316, 37, 139, 272, 185, 192, 218; 128/749, 752, 753, 758, 763, 765, 766

[56] References Cited

U.S. PATENT DOCUMENTS

| | | | |
|---|---|---|---|
| 1,853,260 | 4/1932 | Crossett | 604/218 X |
| 2,052,321 | 8/1936 | Smart | 604/212 |
| 2,511,469 | 6/1950 | Hawks | 604/185 |
| 2,890,699 | 6/1959 | Miller | 604/213 |
| 3,572,340 | 3/1971 | Lloyd et al. | 604/133 |
| 4,058,121 | 11/1977 | Choksi et al. | |
| 4,141,361 | 2/1979 | Snyder | 604/133 |
| 4,182,326 | 1/1980 | Ogle | 604/203 |
| 4,361,155 | 11/1982 | Anastio | 128/763 |
| 4,410,323 | 10/1983 | Hodosh et al. | 604/212 |
| 4,429,693 | 2/1984 | Blake et al. | 604/73 |
| 4,466,446 | 8/1984 | Baidwan et al. | 128/765 |
| 4,660,569 | 4/1987 | Etherington | 128/765 |
| 4,664,128 | 5/1987 | Lee | |
| 4,837,877 | 6/1989 | Massau | 604/272 |
| 4,955,871 | 9/1990 | Thomas | 604/217 |
| 4,967,762 | 11/1990 | DeVries | |
| 4,968,298 | 11/1990 | Michelson | 604/36 |

FOREIGN PATENT DOCUMENTS

| | | | |
|---|---|---|---|
| 0450162 | 10/1991 | European Pat. Off. | 604/133 |
| 0451062 | 10/1991 | European Pat. Off. | |
| 9091 | 10/1894 | Germany | 604/212 |
| 1274282 | 8/1968 | Germany | 604/212 |
| 0178343 | 4/1922 | United Kingdom | 604/192 |
| 1217152 | 12/1970 | United Kingdom | 604/212 |
| 0854397 | 8/1981 | U.S.S.R. | 604/316 |
| 9000072 | 1/1990 | WIPO | 604/216 |

Primary Examiner—John D. Yasko
Assistant Examiner—N. Kent Gring
Attorney, Agent, or Firm—Gunn & Huffner

[57] ABSTRACT

An apparatus for de-airing the heart comprises a clear, resilient bulb fixedly secured to an aspirating needle. The bulb includes a valve which permits air, upon squeezing the bulb, to be discharged therefrom. The aspirating needle includes an axial passage which is closed at the distal end of the needle. One or more longitudinal slots formed in the wall of the needle provide access to the axial passage of the needle for aspirating air from the heart.

3 Claims, 1 Drawing Sheet

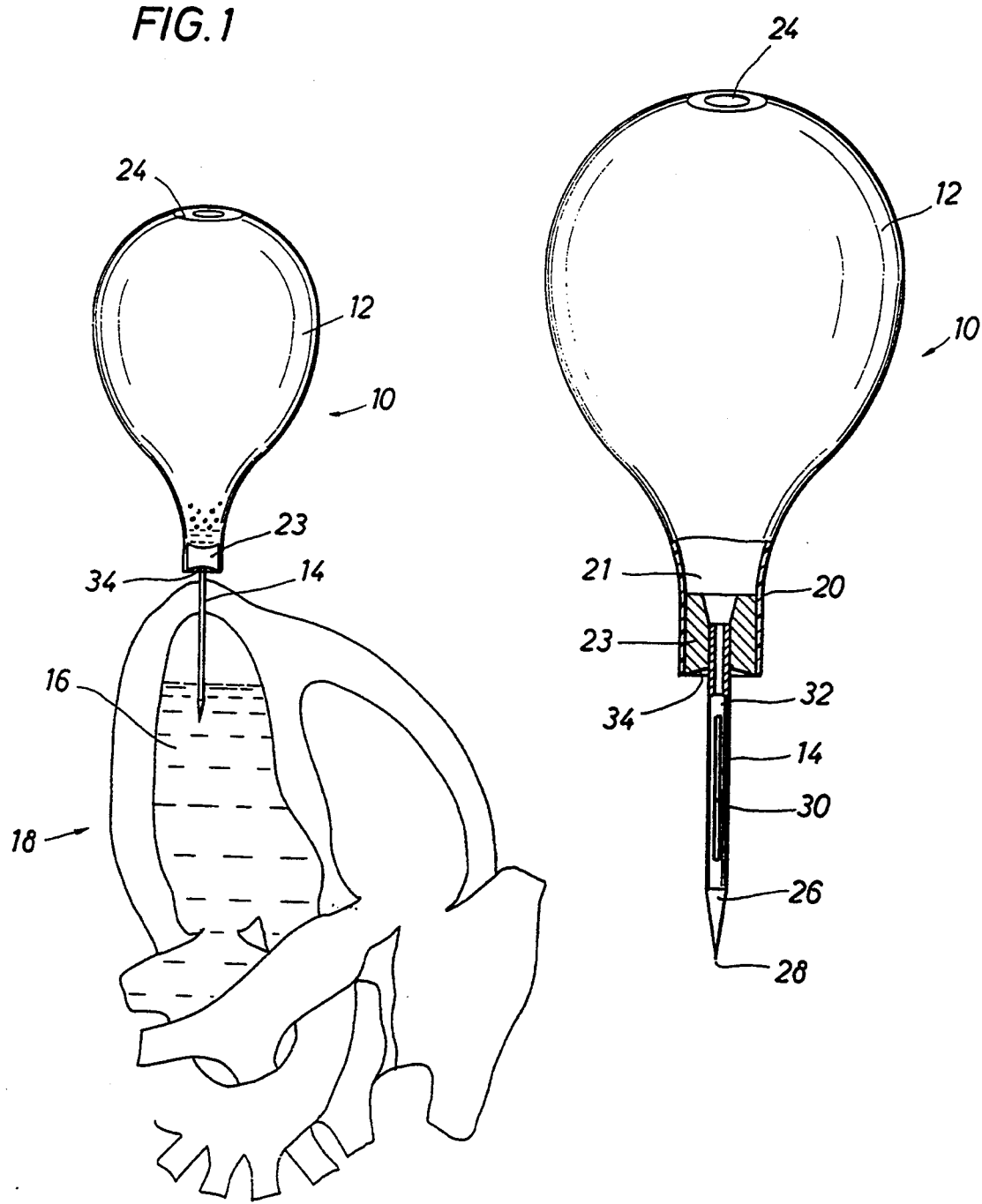

METHOD AND APPARATUS FOR DE-AIRING THE HEART

This is a divisional of U.S. patent application Ser. No. 07/816,115 filed Jan. 2, 1992 (U.S. Pat. No. 5,290,257).

BACKGROUND OF THE DISCLOSURE

This invention relates to an apparatus and method for de-airing the heart, particularly, to a disposable apparatus for aspirating air from the left ventricle of the heart.

Cardiopulmonary bypass surgery is an extremely delicate procedure which saves the lives of many heart patients. A critical step in that procedure involves de-airing the heart after repair of the heart has been completed. If air is not evacuated from the heart, air bubbles in the blood stream could result in stroke or death. Consequently, after completing the repair of the heart and as the cardiac chambers are closed, the heart must be freed of air as much as possible before it begins to beat. Further de-airing maneuvers, however, are also necessary after cardiac action begins. The exact steps in sequences vary from surgeon to surgeon, but the principles are well known in the prior art. These are (1) the filling of the heart with fluid before closing it, to minimize air entrapment; (2) aspiration of residual air from the heart before allowing it to eject; (3) intermittent ventilation of the lungs to express air from the pulmonary veins; and (4) continuous suction on a needle vent in the ascending aorta (or a freely bleeding stab wound) as the heart commences ejecting blood to retrieve any air that may have remained in the heart or pulmonary veins.

All these known methods of de-airing the heart, however, require needle aspiration of the heart to ensure complete evacuation of air from the heart which requires that the heart be gently squeezed repeatedly to force air out of the heart through the needle. Typically, the heart is gently pulled forward and to the right without dislodging it and a needle (usually a 19 gauge injection needle is preferred) is inserted into the apex of the left ventricle. The heart is gently massaged or squeezed as the aspirating needle is reciprocated so that air collected in the left ventricle may be removed through the aspirating needle. It is difficult to determine, however, when the air has been completely evacuated from the heart. Thus, as a cautionary measure, surgeons frequently perform this manipulation many times.

A disadvantage of this known step for de-airing the heart is that it is difficult to properly position the open tip of the aspirating needle within the left ventricle so that air which collects at the top of the left ventricle is aspirated through the needle. This is particularly difficult as the left ventricle fills with blood and the tip of the aspirating needle extends below the level of blood collected in the left ventricle. As the blood level rises, the surgeon must repeatedly move the aspirating needle up and down so that the tip of the needle is above the level of the blood so that air trapped at the top of the left ventricle may be aspirated. This is a rather imprecise procedure which must be repeated many times to insure that substantially all of the air is evacuated from the heart.

Another disadvantage of this known de-airing step is that during diastole of the heart, the heart may suck air into the left ventricle through the aspirating needle. Thus, drawing more air into the heart.

The method and apparatus of the present disclosure overcomes the deficiencies of the prior art methods of de-airing the heart by providing an apparatus which eliminates the required repeated manipulation of an aspirating needle and reduces the extent and duration of manipulation of the heart.

It is therefore an object of the invention to provide an apparatus for de-airing the heart which permits a surgeon to visually determine that the heart is free of air.

It is another object of the invention to provide an apparatus for de-airing the heart by inserting a closed tip needle into the heart and permitting air to aspirate through longitudinal slots formed in the body of the needle.

It is yet another object of the invention to provide an apparatus for de-airing the heart which comprises a resilient squeezable bulb attached to an aspirating needle. The resilient bulb is provided with a valve permitting air to be expelled from the bulb thereby creating a vacuum within the resilient bulb so that air and blood may be sucked out of the heart into the bulb to make the de-airing more efficient and quicker and substantially eliminate any possibility for air being sucked into the heart.

It is another object of the invention to provide an apparatus for de-airing the heart which is sterilized, ready to use and disposable.

SUMMARY OF THE INVENTION

According to one aspect of the invention, the de-airing apparatus comprises a clear, elastic silicone rubber bulb securely attached to an aspirating needle. The bulb includes a one-way valve which permits air, upon squeezing the bulb, to be discharged therefrom. The aspirating needle includes an axial passage which is closed at the distal end of the needle. One or more longitudinal slots formed in the wall of the needle shaft provide access to the axial passage of the needle for aspirating air from the heart.

DETAILED DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is an environmental view, partially in cross-section, depicting the needle of the apparatus of the invention inserted for de-airing the heart; and FIG. 2 is a cross-sectional side view of the apparatus of the invention.

DETAILED DESCRIPTION OF THE PREFERRED EMBODIMENT

Referring first to FIG. 1, the de-airing apparatus of the invention is generally identified by the referenced numeral 10. As shown in FIG. 1, the apparatus 10 comprises a bulb 12 and an aspirating needle 14. In the view of FIG. 1, the needle 14 of the apparatus 10 is shown inserted into the left ventricle 16 of the heart 18. It is understood, however, that use of the apparatus 10 of the invention is not limited to de-airing the heart. The apparatus 10 of the invention may, for example, be used to remove or evacuate fluid from any cavity which may be reached with the needle 14, such as the aorta, vascular graft, etc.

Referring now to FIG. 2, the apparatus 10 of the invention is shown in greater detail. The bulb 12 is preferably oval in shape and fabricated of a clear, elastic silicone rubber. The bulb 12 is transparent permitting the surgeon to see the fluid drawn into the bulb 12. Any air bubbles in the blood collected in the bulb 12 will percolate through the blood and rise to the upper end of the bulb 12. The bulb 12 is provided with a neck 20 at the lower end thereof.

The neck 20 of the bulb 12 is substantially rigid and is provided with an axially disposed opening 21 for receiving the proximal end of the needle 14. The opening 21 of the neck 20 is internally threaded (not shown in the drawing for the sake of clarity) for threaded connection with a threaded end 23 of the needle 14. The needle 14 is securely threaded to the neck 20 so that the surgeon may insert, twist and remove the needle 14 from the heart of a patient without separation of the bulb 12 from the needle 14. Alternatively, the opening 21 may be slightly smaller in diameter than the end 23 of the needle 14 so that the end 23 is frictionally engaged with the neck 20 of the bulb 12, thereby preventing separation therefrom. Other means of securing the bulb 12 to the needle 14, such as clamps, glue, pins or the like, may also be suitable.

The upper or proximal end of the bulb 12 is provided with a valve 24. The valve 24 permits air within the bulb 12 to be expelled therefrom upon squeezing or pinching the bulb 12. The outgoing air ratio is proportional to the pinch speed or force. The valve 24 is a one-way check-type valve which permits air to be expelled from the interior of the bulb 12, but does not permit air to enter the bulb 12 through the valve 24.

Referring again to FIG. 2, the aspirating needle 14 is axially hollow from the proximal end thereof to its solid distal end 26. The end 26 converges to a point 28 so that the needle 14 may be easily inserted into the heart 12. The leading circumferential planar surface 34 of the proximal end 23 of the needle is slightly curved.

The needle 14 is provided with one or more longitudinal slots 30. The slots 30 extend from the end 26 and terminate at a non-slotted portion 32 of the needle 14. In the embodiment of FIG. 2, the two slots 30 are oppositely located along the length of the needle 14. It is understood however that additional slots, three or more, may be formed along the length of the needle 14. The slots 30 however do not substantially weaken the needle 14. The needle 14 is fabricated of material having sufficient rigidity to extend through the wall of the heart 18 without bending or coupling.

The length of the non-slotted portion 32 of the needle 14 is approximately equal to the wall thickness of the heart 18. When the needle 14 is fully inserted in the left ventricle 16 of the heart 18, the leading circumferential planar surface 34 of the proximal end 23 of the needle 14 seals against the outer wall of the heart 18, and the two slots 30 extend from the inner wall of the heart 18 into the ventricle 16. The longitudinal length of the slot 30 permits any air trapped in the ventricle 16 to be aspirated through the needle 14 into the bulb 12.

Use of the apparatus 10 for de-airing the heart 18 is quick, accurate and permits the surgeon to visually determine that the de-airing procedure has been completed. The surgeon holds the heart 18 with one hand while inserting the needle 14 into the heart 18 at the apex of the left ventricle 16 or any other preferred site. The needle 14 is inserted completely into the heart 18 until the leading circumferential planar surface 34 contacts the outer wall of the heart 18. The length of the needle 14 projecting from the neck 20 of the bulb 12 is sufficiently short so that the needle 14 does not extend into the opposite wall of the left ventricle 16. The heart 18 is preferable held upright so that air within the ventricle 16 rises to the top.

To remove the air from the heart 18, the surgeon first pinches the bulb 12 thereby forcing the air out of the bulb 12. The surgeon then inserts the needle 14 into the heart 18 at the apex of the left ventricle 16. As the pinching force on the bulb 12 is slowly released, a vacuum is created within the bulb 12 so that air and blood is sucked out of the left ventricle 16 into the bulb 12. Since the slot 30 extends from the inner wall of the heart 18, air will be sucked out first, then an air/blood mixture and finally some of the blood. As the air/blood mixture enters the bulb 12, the surgeon may observe the air bubbles in the blood to determine when the heart 18 has been completely de-aired. When the air has been completely evacuated from the heart 18, no air bubbles will be observed in the blood sucked into the bulb 12.

Use of the de-airing apparatus 10 and the invention usually requires only a single squeeze of the bulb 12. Occasionally, more air must be evacuated from the heart 18 and several squeezes of the bulb 12 may be required to completely evacuate the air from the heart 18. The bulb 12 is then squeezed and released several times until air bubbles are no longer observed in the blood entering the bulb 12. In this manner, the air is completely removed from the heart 18 without repeatedly reciprocating the aspirating needle and pinching or massaging the heart 18, thereby resulting in minimal damage to the heart. The caliber of the needle 14 is sufficiently small (like a 19 gauge needle) and the solid tip of the needle 14 is extremely sharp. Thus, minimal damage is caused by inserting the needle 14 into the heart 18. The insertion hole formed by the needle is so small that stitches or sutures are not required to close the hole. Blood collected in the bulb 12 may be pumped back into the left ventricle 16 by closing the valve 24 port with a finger before the needle 14 is removed from the heart 18, if desired.

It is will be understood that certain combinations and subcombinations of the invention or of utility and may be employed without reference to other features in subcombinations. This is contemplated by and is within the scope of the present invention. As may possible embodiments may be made of this invention without departing from the spirit and scope thereof. It is to be understood that all matters hereinabove set forth or shown in the accompanying drawing are to be interpreted as illustrative and not in a limiting sense.

While the foregoing is directed to the preferred embodiment, the scope thereof is determined by the claims which follow:

What is claimed:

1. A method of de-airing the heart of a patient, comprising the steps of:
   (a) holding the heart of the patient upright;
   (b) pinching a resilient bulb for substantially evacuating the air therefrom;

(c) inserting an aspirating needle into the left ventricle of the heart, wherein said aspirating needle includes an axially hollow body terminating in a solid tip at one end and connected to said transparent resilient bulb at an opposite end, and wherein said body of said aspirating needle includes a longitudinal slot extending substantially the entire length between said solid distal end and said opposite end of said needle body; and (d) slowly releasing the pinching force applied to said bulb for aspirating fluid from the heart.

2. The method of claim 1 including the step of pumping the blood collected in said bulb back into the heart.

3. The method of claim 1 including repeating steps (b) and (d) until air bubbles are no longer observed in the fluid removed from the heart.

* * * * *